United States Patent [19]

Olsen

[11] Patent Number: 4,600,384
[45] Date of Patent: Jul. 15, 1986

[54] SWIVEL COUPLING FOR ILLUMINATED DENTAL HANDPIECE

[75] Inventor: Robert A. Olsen, Palatine, Ill.

[73] Assignee: Sybron Corporation, Rochester, N.Y.

[21] Appl. No.: 656,035

[22] Filed: Sep. 28, 1984

[51] Int. Cl.⁴ ............................................. A61C 3/00
[52] U.S. Cl. ..................................... 433/29; 433/126
[58] Field of Search ................................. 433/29, 126

[56] References Cited

U.S. PATENT DOCUMENTS

| | | | |
|---|---|---|---|
| 4,260,382 | 4/1981 | Thomson | 433/126 |
| 4,334,863 | 6/1982 | Magid et al. | 433/29 |
| 4,403,959 | 9/1983 | Hatakeyama | 433/126 |
| 4,460,337 | 7/1984 | Landgraf | 433/29 |
| 4,514,169 | 4/1985 | Strohmaier | 433/29 |
| 4,518,355 | 5/1985 | Hoffmeister et al. | 433/29 |

FOREIGN PATENT DOCUMENTS

| | | | |
|---|---|---|---|
| 0070194 | 1/1983 | European Pat. Off. | 433/29 |
| 1068425 | 11/1959 | Fed. Rep. of Germany | 433/29 |
| 1161157 | 8/1958 | France | 433/29 |

Primary Examiner—John J. Wilson
Attorney, Agent, or Firm—Robert A. Gerlach; Robert J. Bird

[57] ABSTRACT

A swivel coupling for connection between a dental handpiece and a supply hose. The coupling includes a lamp in its handpiece connector portion, and an annular commutator in its hose connector portion. The lamp base is in sliding contact with the commutator to permit swiveling of handpiece portion relative to hose portion. Exhaust air from the handpiece turbine meter passes over and around the lamp and its surrounding structure for heat removal.

1 Claim, 2 Drawing Figures

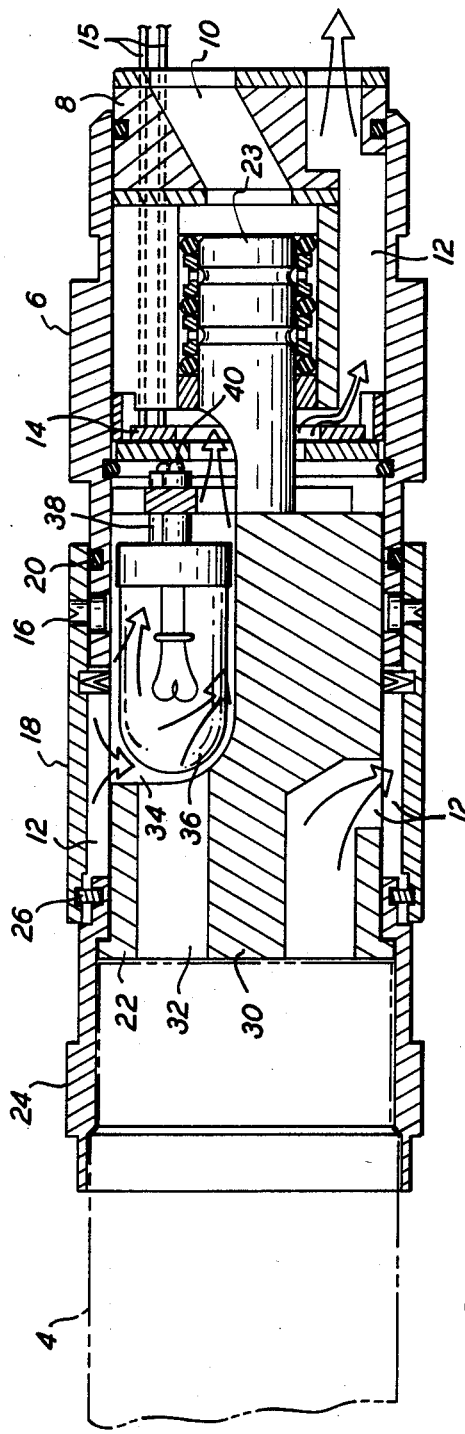
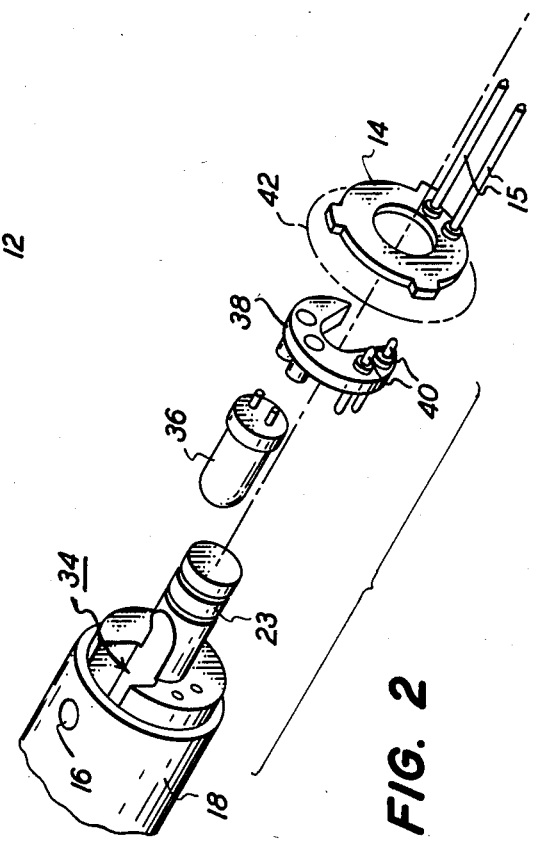
FIG. 1
FIG. 2

4,600,384

SWIVEL COUPLING FOR ILLUMINATED DENTAL HANDPIECE

BACKGROUND AND SUMMARY OF THE INVENTION

The subject matter of this invention is a swivel coupling for connecting a hose containing a plurality of conduits to a handpiece such as a dental handpiece having like conduits for drive air, secondary air and water. In addition, the coupling of this invention includes a lamp for illumination of the handpiece work area, such lamp being adapted for swivel connection to electrical conductors extending through the hose.

The most relevant prior art that I know of is U.S. Pat. No. 4,398,885, issued Aug. 16, 1983 to Loge and Bareth. This patent discloses a dental handpiece including an illumination lamp for illuminating an optical fiber bundle which in turn illuminates the work area. The handpiece is swiveled relative to to its connection to a supply hose. The lamp appears to be stationary with respect to the hose coupling and the handpiece is rotatable relative to the lamp.

The present invention may be summarized as a dental handpiece swivel coupling with a handpiece portion attached to the handpiece and a hose portion attached to a supply hose, the handpiece portion being swivelably mounted on the hose portion. The handpiece portion of the coupling includes an illumination lamp which makes electrical contact with an annular commutator on the hose portion, electrical continuity thus being maintained while the handpiece portion of the coupling swivels relative to the hose portion of the coupling. Exhaust air from a turbine in the handpiece is directed over the lamp for heat removal.

DRAWING

FIG. 1 is a side sectional view of a handpiece coupling according to this invention.

FIG. 2 is an exploded view of some of the internal elements of FIG. 1.

DESCRIPTION

With reference now to the drawing, the swivel coupling of this invention is generally indicated at 2 and is shown attached to a handpiece indicated in phantom lines at 4 at the left end of the coupling. The right end of the coupling is connected to a supply hose, not shown, which supplies air, water and electrical wiring to the coupling. The handpiece swivel coupling 2 may be considered as including a hose connector portion and a handpiece connector portion, one being rotatable or swivelable relative to the other.

The hose connector portion of coupling 2 includes a hose connector ring 6 which is adapted for threaded engagement with the supply hose. Connector ring 6 carrys the ported body of a hose adaptor 8 which includes passages 10 and 12 for drive air and exhaust air respectively, such passages being in registry with corresponding conduits in the supply hose. The hose connector portion of the coupling also includes an annular commutator ring 14 which is electrically connected by elongated pins 15 to a source of electrical current supplied through the supply hose. The connector ring 6 is detachably connected by a bayonet fitting 16 to a disconnect ring 18. An O-ring 20 mounted on connector ring 6 forms a sealing engagement with the interior of the disconnect ring 18.

The handpiece connector portion of coupling 2 includes a swivel tube 22 which includes a drive air passage (not shown) and exhaust air passage 12 in registry with corresponding passages in the handpiece 4. Swivel tube 22 is surrounded by a handpiece connector ring 24 by which the coupling device is threaded to the handpiece 4. The disconnect ring 18 is rotatably mounted to the handpiece connector ring 24 by means of a locking ring 26. Swivel tube 22 further includes an axially extending cylindrical spool 23 which has a pair of sealed annular grooves communicating with air and water ports in the hose adaptor 8, and which spool 23 is internally ported to continue the water and air passages through swivel tube 22 and into corresponding conduits in handpiece 4.

With the device assembled as described, the handpiece connector ring 24, swivel tube 22 and spool 23 are rotatable relative to hose connector ring 6, hose adaptor 8 and disconnect ring 18.

Swivel tube 22 includes a body 30 of thermally conductive material such as aluminum, body 30 in turn defining the passages for drive air (not shown), exhaust air 12, and a light aperture 32 which is in registry with an optical fiber bundle in the handpiece 4, which in turn directs light onto the handpiece work area. A lamp cavity 34 is also formed in the conductive body 30. Lamp cavity 34 communicates with the annular cavity 12 which forms a part of exhaust air passage 12. A lamp 36 is mounted within lamp cavity 34 to illuminate the light aperture 32 and the corresponding optical fiber bundle extending through the handpiece. Lamp 36 is inserted into a base 38 which includes spring loaded commutator contacts 40 in slidable electrical contact with commutator 14. Thus electrical continuity to the lamp 36 is maintained throughout swiveling or rotation of the handpiece and the handpiece portion of the coupling relative to the hose and the hose portion of the coupling.

FIG. 2 shows in exploded view the electrical and lamp components of FIG. 1. FIG. 2 also shows more clearly the location of the swivel plane 42, between lamp base 38 and commutator 14.

In operation, air is supplied to an air turbine at the head end of the handpiece 4, exhaust air returning from the handpiece 4 through exhaust air passage 12. As will be seen from the drawing, exhaust air passage 12 includes an annular portion surrounding the body 30 and communicating directly with the lamp cavity 34. Exhaust air from the turbine is thus directed over the lamp, over the lamp contacts, and over the conductive body 30 which acts as a heat sink. From the base of lamp 36, exhaust air continues through passage 12 back through the hose connector portion of the coupling and into the supply hose.

Separation of the swivel coupling at the disconnect ring 18 and bayonet fitting 16 provides access to the lamp base 38 and lamp 36. Simply by grasping the base 38, the lamp can be removed from its cavity 34. Once lamp and base are removed, the lamp 36 is easily removable from the base 38 for low cost lamp replacement. In other words, the lamp 36 can be replaced when necessary without replacing the base 38. Conversely, the base 38 is individually replaceable.

Electrical insulation is provided at required areas within the electrical system by hard coat anodizing of the various parts, which are made of an aluminum alloy.

What is claimed is:

1. A swivel coupling device for connection between a dental handpiece and a supply hose, said coupling including:
- a hose-connector portion defining passages for air and water and adapted for releasable connection to said hose in registry with corresponding air and water conduits therein,
- a handpiece-connector portion defining passages for air and water and adapted for releasable connection to said handpiece in registry with corresponding air and water conduits therein, said handpiece-connector portion further defining a lamp cavity displaced from the axis of said coupling and in registry with an optical fiber bundle in said handpiece, said lamp cavity being a part of the flow path of exhaust air from said handpiece,
- said hose-connector portion and said handpiece-connector portion being releasably and swivelably connected to each other,
- an annular electrical commutator ring operatively and removably mounted to said hose-connector portion and facing the swivel interface of said coupling, and
- a lamp removably mounted to a lamp base which is in turn removably mounted to said handpiece-connector portion so that said lamp is disposed within said cavity for illumination of said fiber bundle, said lamp base including spring loaded commutator brushes extending axially of said coupling for sliding contact with said commutator ring at the swivel interface of said coupling.

* * * * *